(12) United States Patent
Kim et al.

(10) Patent No.: US 7,192,775 B1
(45) Date of Patent: Mar. 20, 2007

(54) PATHOGENESIS RELATED PROTEIN AND USE THEREOF

(75) Inventors: Young Soon Kim, Gwangju (KR); Ae Ran Park, Gwangju (KR); Moon Kyung Ko, Jeonam (KR); Jae Bok Yoon, Gyeonggi (KR); Hyo Guen Park, Seoul (KR); Pill-Soon Song, Gwangju (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 0 days.

(21) Appl. No.: 11/249,345

(22) Filed: Oct. 14, 2005

(51) Int. Cl.
*C12N 15/82* (2006.01)
*C12N 5/10* (2006.01)
*C12N 15/74* (2006.01)
*C07H 21/04* (2006.01)

(52) U.S. Cl. ............... 435/468; 536/23.6; 435/320.1; 435/419; 435/471

(58) Field of Classification Search .................... None
See application file for complete search history.

(56) References Cited

OTHER PUBLICATIONS

2001 GenBank Accession No. AF244121.*

* cited by examiner

*Primary Examiner*—Ashwin Mehta
*Assistant Examiner*—Li Zheng
(74) *Attorney, Agent, or Firm*—Jacobson Holman PLLC

(57) ABSTRACT

The invention relates to a gDNA and corresponding cDNA sequence comprising pathogenesis related protein-10 (CbPR-10) gene in *Capsicum baccatum*. The polypeptide encoded by the DNA sequence has ribonuclease activity which makes the enzyme highly effective in inhibiting the growth of fungal pathogen. The use of the DNA sequence disclosed herein contains the gDNA, cDNA, protein and a genetic construct for the production of transgenic plants, especially genetically transformed pepper plants, with an enhanced resistance against fungal pathogens.

5 Claims, 9 Drawing Sheets

```
AAGCTTCTTAAAACAGTATATCCATGAATCTGCTTGACTTGTTTCATGTCATTTTCTCAA   -1095
TCATCAAAGAACTCAACAATCTTTAATGTCATGCACACAATAAATTTTGAGTATGAATAT   -1035
CTAATTTAAAGAAAAAATTATATTTAATTAGTGCAAGATTTTACATATTTTTATTTATAA   -975
CAGCTAAATAGAAAATTTGAACGTCAAACGTTTTACATATATAATAGTAGCTCTCTATAG   -915
CAACAG TTCTAAATTTTTAAATATACATTATCATTATAAAGAGGTTTTACTGTATAAATA  -855
AAAATCTCGATCAAAACATCATTAAATGCAAACTCATGAGACTGTAGCATTCATCTTTTG   -795
AATGATAGTAATAAATAATTTTGAATTCTAGCTGTTCATACCATATACTGAGAATAATAT   -735
CAGCCTACCACTATTGAAAACCAAGTTGATAGGTTCCCACAGTCTACATCAACTTAATAT   -675
CGTGTCAGCAAATCTTATTGTTATTTATCATTTGGCATAAAATTCTCTCAATATGTATCA   -615
TGACTAACAAATTAATTATGGCACAACATCTAGAAGAAAGAAAAACTGAACCCAAATGTC   -555
AGCAATGGAGTGCTTTGAATGTTGAAATTAAGACTAAATTAAGGTTGCTCAAGAGTGAAC   -495
TCTAAGGGTGTGCTTGGTATGTATGAGAGAAAAACATTTTCAATCAAATAATATTTTCTT   -435
CAAAAATAAGTGGGGTTTTTCGTGTCTTGACAAAAATGTATAAAAATATTATCCAAATAT   -375
ATTTATATATTTTTTCTTTTAGATCATGTTAAGTGAATTGTTGAGATCTTAATCCTATTT   -315
TTTGAAAAATAGACTATTTTCAATACACTTTTGATTTAAGTAAAACATTTTAAATCGAAC   -255
TTGAAAAGAAAATACAATAATGAAGATATCATATTAAAAAAAAAAAAAAGAAATTTGTTT   -195
TTCTAAGAGAATATTAATTTTGACTAACTAAACAATCATGTGAAGAATTTTCAAACACAC   -135
CCTAAAATCTCACTACATTTTATCACTATAAATACCATCTAAAAACTCCCATATATCACA   -75
CACCTCAAAACATTACAATCATCTTATCCTAAGCTCTTTCTTCTTCTTGTTTAAGGCAAA   -15
TTAATCAAAGCATTATGGGTGCCTATACCTTTACTGACAAGTCCACAGCCTCAGTTGCCC    46
              M   G   A   Y   T   F   T   D   K   S   T   A   S   V   A
CATCAAGGCTATTCAAAGCTTTGGTTATTGATTTTAACAACATTGTATCTAAATTGGCAC    106
 P   S   R   L   F   K   A   L   V   I   D   F   N   N   I   V   S   K   L   A
CTGATGTTAAGAGTATTGAGAATGTTGAAGGTGATGGTGGTGCTGGAACCATCAAGAAGA    166
 P   D   V   K   S   I   E   N   V   E   G   D   G   G   A   G   T   I   K   K
TGACCTTTGTCGAAGGTTTGTTTTTATTTTTTTTGAGGTGCGATATTCATATTAAAGG     226
 M   T   F   V   E   G
TCGGTTATTAGTAGCCAAAATTGATACACGTGAAATTTTGTCAGAATATTTTTGAATAAG    286
ACATTTTTTTAATTTGATATTTGTATATAGCGATCATAATAAAGAAAACAGTTTTATAA    346
GGTACTAAAAATTATACAAGAACAAATAAATTAATTGGACAAATTTGATTGTGACTCCCA    406
TTTTAATCCATATCAATCCAATTATGGACGGCTCAAAACCTACTTATATATTTACTTAAC    466
CTATTTTGATCTGTCCAAATTCAATCCATTCCGCTCATTTAATACTTCTATCAATAAATA    526
TCCATTGAAGGATCATTTTAATAGAAAAATTATTTACCTTAATATATGAAACTTAATGT    586
TTTTTATTAATGACAGGTGGTCCAATAAAGTACATGAAGCACAAGATTCATGTGATTGA    646
              G   P   I   K   Y   M   K   H   K   I   H   V   I   D
CGAAAAGAATTTAGTAACAAAATATTCACTTATCGAAGTGATGTTCTTGAAGGCAAAGC    706
 E   K   N   L   V   T   K   Y   S   L   I   E   S   D   V   L   E   G   K   A
AGAATCAGTTGATTATGATGGCAAATTTGAAGCTTCTGCAGATGGAGGATGTGTTTGCAC    766
 E   S   V   D   Y   D   G   K   F   E   A   S   A   D   G   G   C   V   C   T
CACAGTAACTGTGTACAACACAAAAGGTGATTATGTTGTTACTGAGGAAGAACACAATGT    826
 T   V   T   V   Y   N   T   K   G   D   Y   V   V   T   E   E   E   H   N   V
GCACAAAGACAAAGCCAATGACCTTCTCAAGGCCATCGAAGCATACCTCCTCGCCAATCC    886
 H   K   D   K   A   N   D   L   L   K   A   I   E   A   Y   L   L   A   N   P
TTCTGTCTGTGTTTAAGCCAATGACCTTGCTGTGATGTTATATAGTTAAATAATTATAAG    946
 S   V   C   #
TGTGTCATGTTTAAGAAGTTTAAAGTTTTTAGATGAGAGGAAAAAATAAGATTGATTATG   1006
TATGGGTTGTATCAGTTCTTCTAAGGGATTGAGTTTTGGG                       1046
```

FIG. 2

```
C. annuum    MGAYTFTDKSTASVAPSRLFKALVIDFNNLVSKLAPDVKSIENVEGDGGAGTIKKMTFVE    60
C. baccatum  MGAYTFTDKSTASVAPSRLFKALVIDFNNIVSKLAPDVKSIENVEGDGGAGTIKKMTFVE    60

C. annuum    GGPIKYMKHKIHVIDEKNLVTKYSLIESDVTENKAESVDYDGKFEASADGGSVCTTVTVY   120
C. baccatum  GGPIKYMKHKIHVIDEKNLVTKYSLIESDVLEGKAESVDYDGKFEASADGGCVCTTVTVY   120

C. annuum    NTKGDYVVTEEEHNVHKEKANDLLKAIEAYLLANPSVYV  159
C. baccatum  NTKGDYVVTEEEHNVHKDKANDLLKAIEAYLLANPSVCV  159
```

☐ : prediction for phosphrylation sites

— : P-loop

FIG. 3

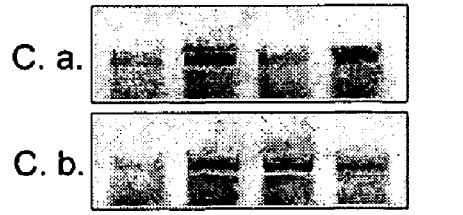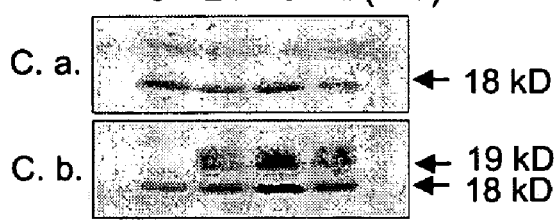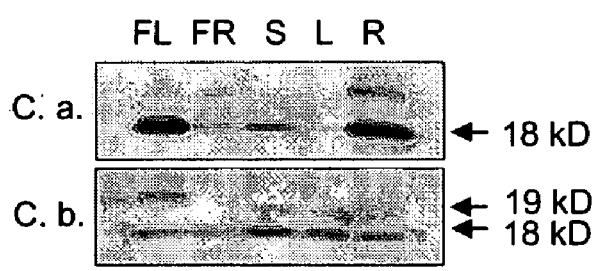
FIG. 4

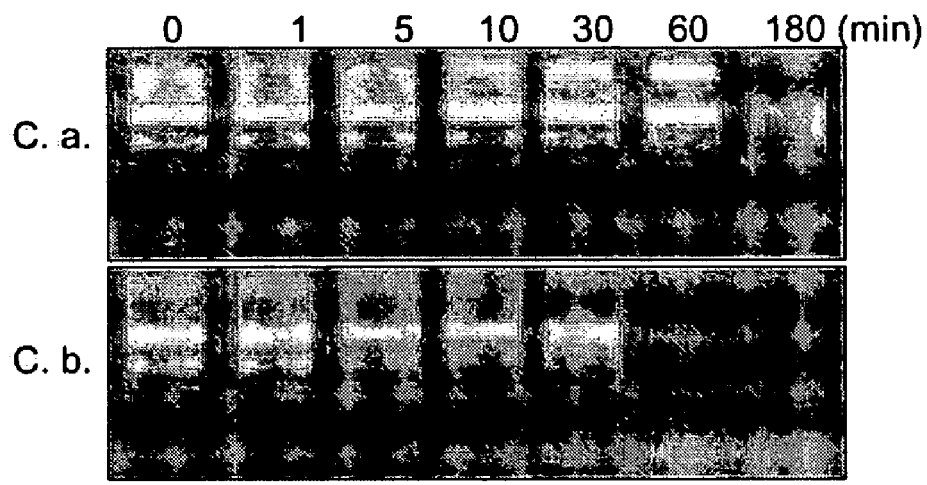
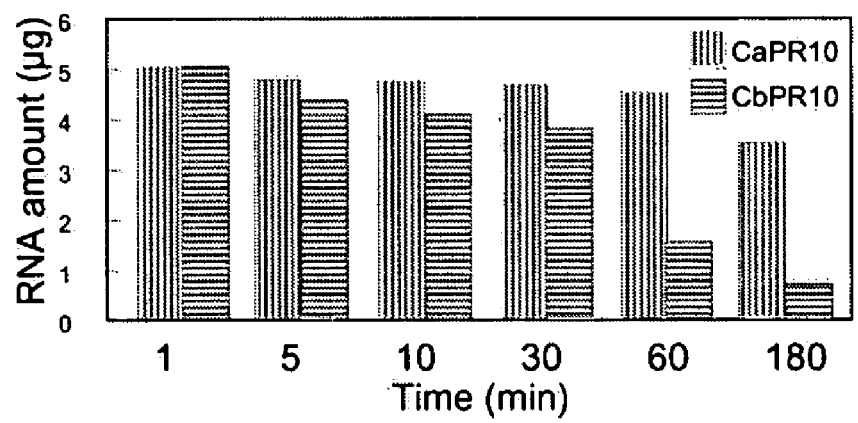
FIG. 8

PATHOGENESIS RELATED PROTEIN AND USE THEREOF

BACKGROUND OF THE INVENTION

1. Field of the Invention

The present invention relates to the DNA sequences encoding a pathogenesis related-10 (CbPR-10) protein from *Capsicum baccatum*. The gDNA contains a novel nucleic acid sequence for a promoter. The polypeptide of CbPR-10 shows weak ribo-nuclease activity, which becomes stronger after fungal induced phosphorylation of the protein. The invention also relates to the sequences comprising the cDNA sequence fused with invented or other appropriate promoter and terminator in a genetic construct for transformation of plants or industrial use. Such an expression of the genetic construct in plant results in an increased resistance to phytopathogenic fungi, especially anthracnose fungus.

2. Description of Prior Art

Plants respond to the invasion of phyto-pathogens by coordinated and integrated set of metabolic alterations. To resist the pathogen, various genes are induced at the infection site and distal part of the plant in association with the development of hypersensitive reaction (HR) and systemic acquired resistance (SAR), respectively. These genes include pathogenesis-related (PR) and antibiotic proteins, etc.

The PR proteins are a class of proteins that are synthesized in plants in response to pathogenic infection. Usually, PR proteins are not present in healthy plants, but are synthesized in response to pathological or related stresses. In the latest proposition, PR proteins are divided into 14 families based on their sequences, serological properties, and biological activities. When most PRs are extra-cellular proteins, PR-10 is the first described intracellular protein in cultured parsley cell upon elicitor treatment. It has been supposed that the intracellular PR-10 is capable of cleaving viral RNA or other pathogen's RNA in the plant cells. According to Park et al., (2004), CaPR-10 protein, isolated from *Capsicum annuum*, is phosphorylated upon TMV-$P_0$ inoculation and functions as a kind of RNase being able to cleave viral RNA. Also, recombinant CaPR-10 inhibited oomycete growth as well as viral infection. So, it has been suggested that cytosolic phosphorylated PR-10 protein is an active component of an inducible-defense mechanism against pathogen infection.

A majority of cultivated pepper lines have been developed from *C. annuum* species which are very susceptible to anthracnose fungus. A pathogenic agent of anthracnose disease, *Colletotrichum acutatum*, causes the most destructive disease in widely cultivated pepper varieties and results in serious economical loss. By anthracnose fungus, most serious damage occurs in the fruit of pepper. This pathogen becomes necrotrophic after penetration into the epidermal cells, so that fungal hyphae colonize intracellularly in sub-cuticular tissues of the fruit. Since PR-10 localizes in the cytoplasm of the plant cell, it will be valuable to examine the inhibitory effect of PR-10 protein during the fungal infection. So, we isolated and characterized a PR-10 gene from *C. baccatum* that showed incompatible interaction with anthracnose fungus. Also, relative ribonuclease and antifungal activity were compared with previously reported CaPR-10 protein of the susceptible species, *C. annuum*.

There are a few *Capsicum* accessions, such as *C. baccatum* and *C. chinense* species, showing resistance to anthracnose fungus. If defense related genes of resistant species are available, it will provide opportunities to transfer the genes into susceptible species. Recently, genetic engineering techniques are offering relief from the destructive disease in cultivated pepper lines through the development of fungus control systems using resistance related genes isolated from fungal resistant species. Ultimately, biotechnological applications of CbPR-10 protein may provide agronomically relevant level of disease control on pepper cultivation without harmful side effects.

SUMMARY OF THE INVENTION

This invention relates to a cDNA clone of SEQ ID NO: 1 from *Capsicum baccatum*, designated as pathogenesis related protein 10 (CbPR-10) of SEQ ID NO: 2. The fruits of *C. baccatum* are resistant to the anthracnose fungus, *Colletotrichum acutatum*. However, most commercial pepper varieties are developed from *C. annuum*, which is very susceptible to the fungus. Until now, no commercial cultivars resistant to the anthracnose have been developed. In this work, since anthracnose fungi colonize in the cuticular cells of the fruit, an intracellular pathogenesis related protein, PR-10, was cloned from resistant pepper species to clarify the functional relationship in the incompatible reaction of the fruit with the fungus.

Deduced amino acid sequence of CbPR-10 showed 96% identity with that of CaPR-10 from *C. annumm* species and contained P-loof conserved among PR-10 proteins. But, a few putative phosphorylation sites are differed from that of CaPR-10. The phosphorylated CbPR-10 protein with a predicted size of 19 kDa was clearly detectable in coincidence with 18 kDa in infected fruits of *C. baccatum*, while only 18 kDa is detectable in that of *C. annuum*. Immunohistochemical examination revealed that PR-10 accumulation was localized in epidermal cells and a few layer of subcuticular cells of the unripe fruits. After infection, protein accumulation markedly increased in both cells layers, especially in the fruits of *C. baccatum*. The expression of CbPR-10 genes was induced by fungal infection, but expression level was much higher in *C. baccatum*. Characterization of the enzymatic properties indicated that the recombinant CbPR-10 protein exhibits stronger ribonucleolytic activity rather than CaPR-10 protein and also showed better antifungal activity to anthracnose fungus.

Regulatory sequences may be useful in controlling temporal and/or spatial expression of a gene. So, identification of promoters which are active in infection site is of interest. A potential source for pathogen inducible promoters is the pathogenesis-related (PR) family of defense-related genes. Typically, PR proteins are expressed the infection site of plant tissues in response to the pathogen. In this experiment, nucleic acid sequences comprising the regulatory region of pathogenesis related protein 10 was isolated and characterized by the ability to regulate expression of CbPR10 gene.

BRIEF DESCRIPTION OF THE DRAWINGS

FIG. 2. Deduced amino acid sequences of SEQ ID NO: 2 and nucleotide sequence of gDNA of pathogenesis related 10 protein (CbPR-10) isolated from *Capsicum baccatum* (SEQ ID NO: 9).

FIG. 3. Alignment of the deduced amino acid sequences of CbPR-10 of SEQ ID NO: 2 with CaPR-10 of SEQ ID NO:

4. The CbPR-10 encoded polypeptide is aligned to pathogenesis related 10 protein (CaPR-10) from *Capsicum annuum* (GeneBank No. AF244121). P-loop motif is underlined and putative phosphorylation sites are enclosed by square. Sequence variations between two species are aligned and marked.

FIG. 4. Gene expression (A) and protein accumulation (B) of CaPR-10 and CbPR-10 in the fruits from their respective pepper species inoculated with anthracnose fungus. In A, total RNA was prepared from fruits at 0, 24, 48, and 72 HAI and 100 ng of total RNA was used as template for RT-PCR analysis. In B, immunoblot analysis of PR-10 protein (2 μg) was conducted in infected pepper fruits. Soluble proteins were extracted from infected fruits with anthracnose fungus at 0, 24, 48, and 72 HAI. The polyclonal antibody raised against the recombinant CaPR-10 was used at 1:1500 dilution and HRP-conjugated anti-rat IgG antibody was used as the secondary antibody at 1:5000 dilution.

Figure 5:
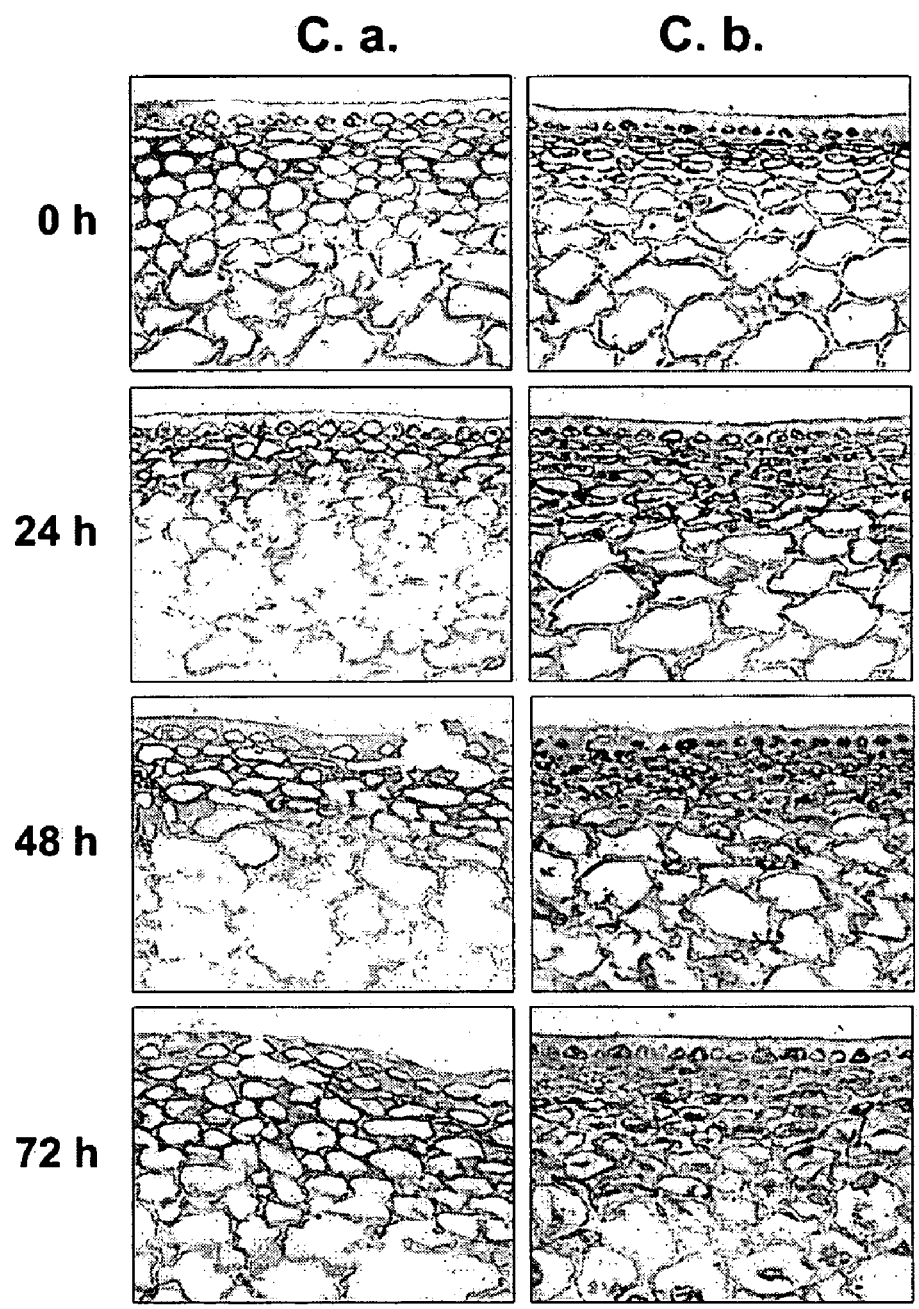

FIG. 5. Immunolocalization of CaPR-10 and CbPR-10 proteins in infected fruits of susceptible and resistant species, *C. annuum* and *C. baccatum*, respectively. The pepper fruits were inoculated with *C. acutatum* and prepared samples from the inoculation sites at 0, 24, 48, 72 HAI. The sections were incubated with polyclonal antibody against the recombinant CaPR-10 and detected with peroxidase labeled secondary antibody. The localization of PR-10 protein is detected by a red color. Control experiments using pre-immune serum did not show any reactions (data not shown). A bar represents 100 μm.

Figure 6:
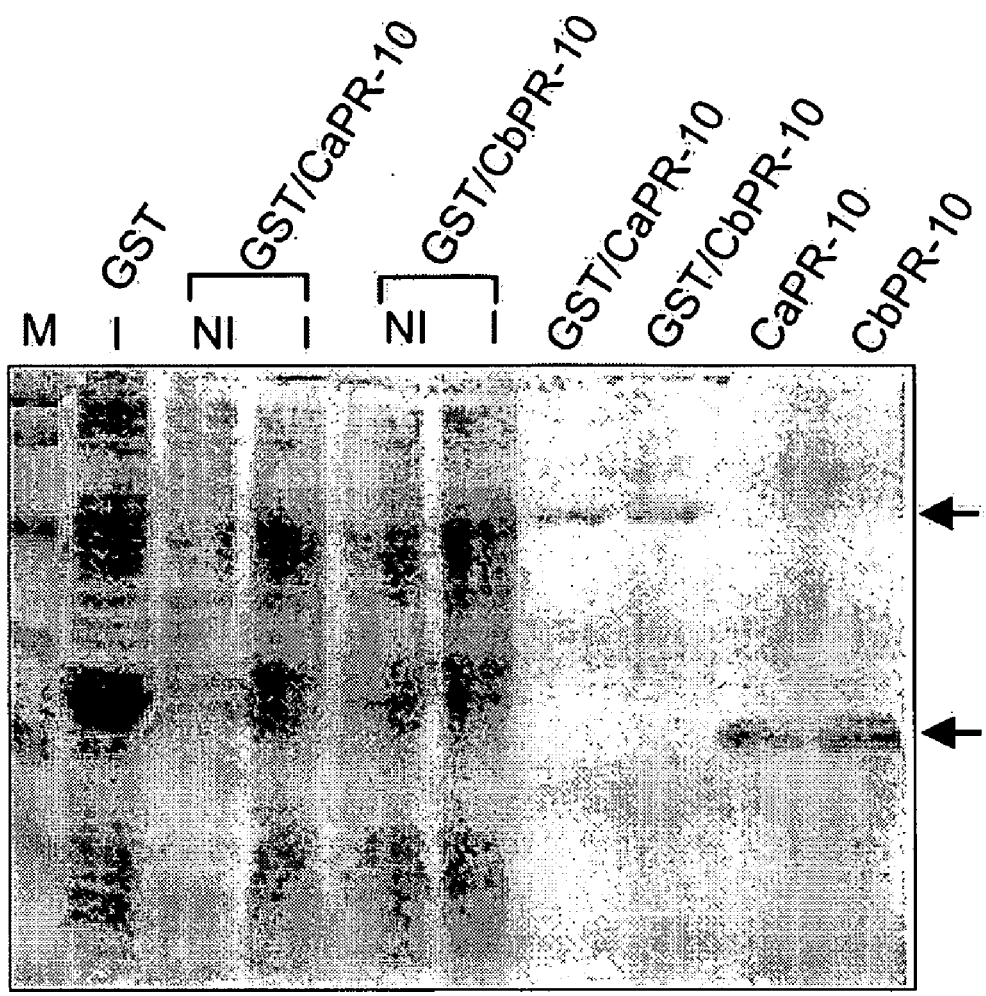

FIG. 6. Expression and purification of recombinant CaPR-10 and CbPR-10 proteins. SDS-PAGE analysis of the recombinant PR-10 proteins produced in *E. coli* at different steps of purification. Lane M, Protein molecular weight markers (size: kDa). From the left, lane 1, soluble fraction of *E. coli* BL21 cells carrying pGEX6p-1 plasmid that codes for GST protein; lane 2, soluble fraction of *E. coli* with pGEX6P-1/CaPR-10 codes for GST-CaPR-10 protein, grown without IPTG; lane 3, same as lane 2, but induced with IPTG; lane 4, soluble fraction of *E. coli* with pGEX6P-1/CbPR-10 codes for GST-CbPR-10 protein, grown without IPTG; lane 5, same as lane 4, but induced with IPTG; lane 6, purified GST/CaPR-10 fusion protein; lane 7, purified GST/CbPR-10 fusion protein; lane 8, cleavaged CaPR-10 protein; lane 9, cleavaged CbPR-10 protein.

Figure 7:
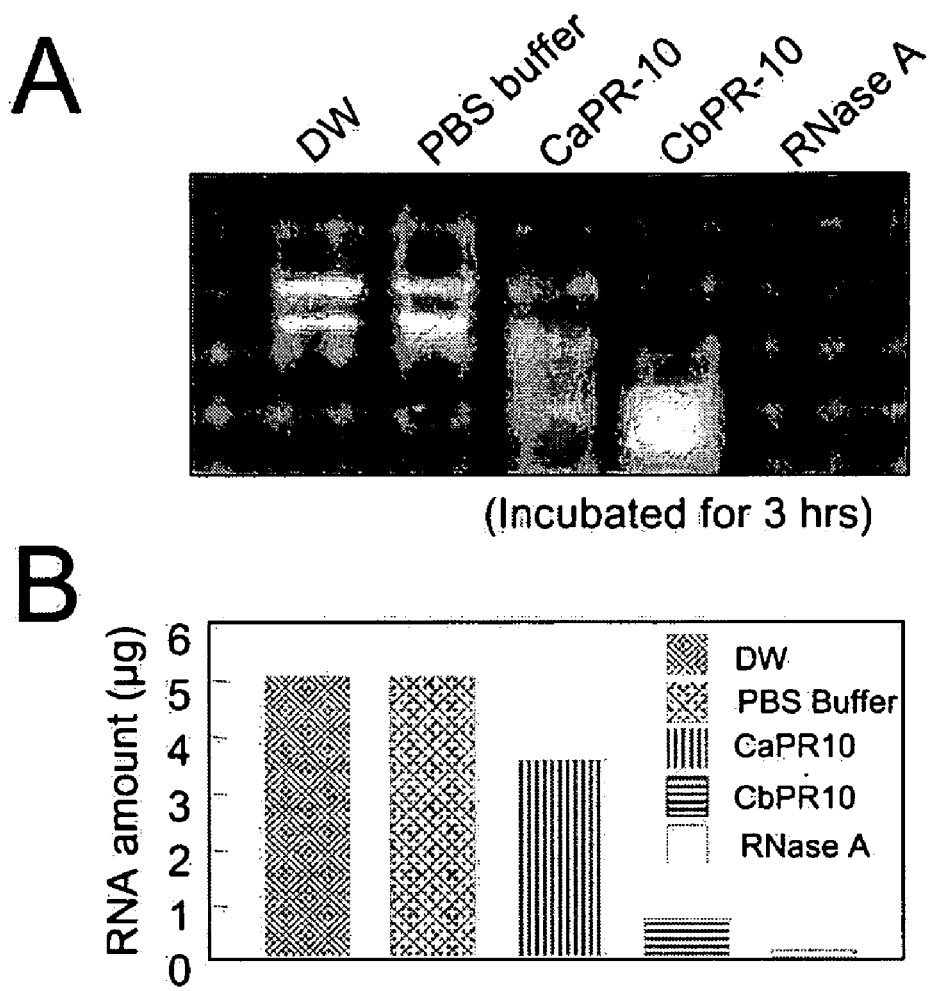

FIG. 7. Ribonucleolytic activity of recombinant PR-10 proteins against pepper total RNA. Each reaction mixture contained 5 μg of total RNA from pepper fruits and incubated for 3 hours at 56° C. Hydrolyzed RNAs were separated in 1.0% agarose gels. Lane 1, RNA+distilled water; lane 2, RNA+protein elution buffer; lane 3, RNA+CaPR10 protein (2 μg); lane 4, RNA+CbPR10 protein (2 μg); lane 5, RNA+RNase A (SIGMA, USA). Relative levels of RNA were shown in the bar graphs underneath.

FIG. 8. Time course of RNA degradation by ribonucleolytic activity of recombinant PR-10 proteins against pepper total RNA. Each reaction mixture contained 5 μg of total RNA from pepper fruits and incubated for 3 hours at 56° C. Hydrolyzed RNAs were separated in 1.0% agarose gels. Upper gel, RNA+CaPR-10 (2 μg); lower gel, RNA+CbPR-10 (2 μg). Relative levels of RNA were shown in the bar graphs underneath.

Figure 9:
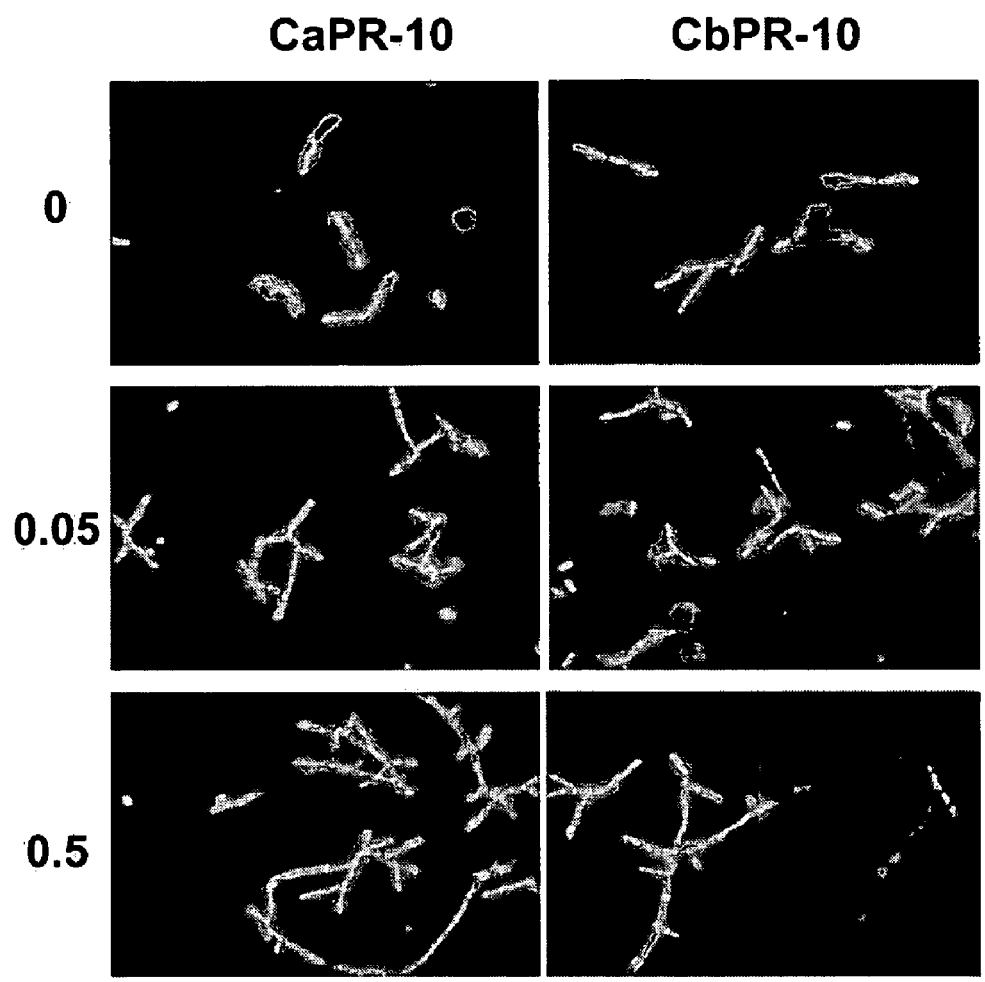

FIG. 9. Microscopical observation of an in vitro fungal inhibition assay at 24 hours after addition of recombinant PR-10 proteins to the spore of anthracnose fungus. Viability of the fungus was determined by using Live/Dead bacterial viability kit (Molecular probe, USA). Left panel: recombinant CaPR-10 protein was added at 0, 0.05, and 0.5 mg/L. Right Panel: recombinant CbPR-10 protein was added at 0, 0.05, and 0.5 mg/L.

DETAILED DESCRIPTION OF THE INVENTION

Figure 1:
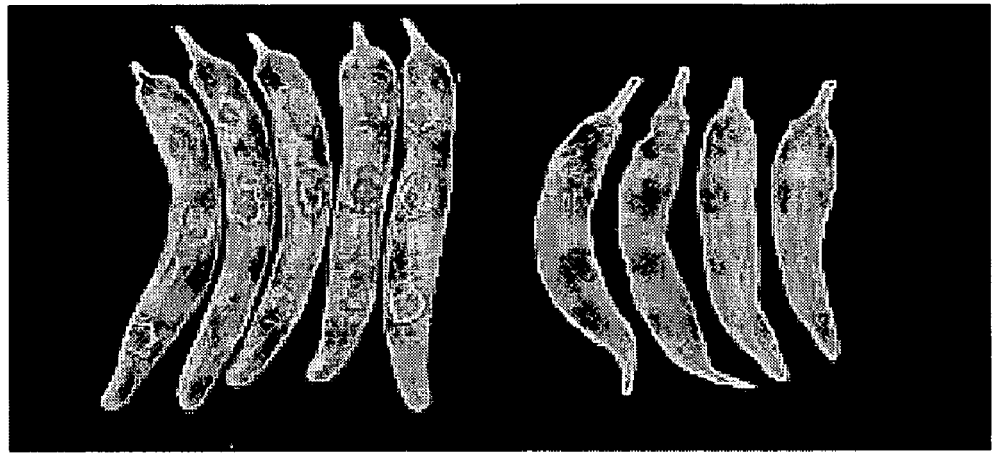
FIG. 1. Anthracnose symptoms developed on susceptible and resistant pepper fruits, *Capsicum annuum* cv. Yeo-ju and *Capsicum baccatum* cv. PBC80, respectively, at 7 days after inoculation with KSCa-1 isolate of *Colletotrichum acutatum*.

The present invention provides a cDNA clone, designated as CbPR-10, which was isolated from infected unripe fruits of *C. baccatum* showing incompatible interaction with *C. acutatum* (FIG. 1). Thus, gDNA sequence corresponding CbPR-10 was cloned from *C. baccatum*. The sequence was comprised of the promoter of SEQ ID NO: 3 and coding region of CbPR-10 gene. The promoter contains transcriptional initiation site, which favor the initiation of transcription in infected tissues (FIG. 2). Then, full-length of cDNA was cloned of which contains an open reading frame of 480 bp from the the first translation start (ATG) at nucleotide position 1 to a translational stop (TGA) at position 478. The nucleotide sequences of CaPR-10 encode a polypeptide of 159 amino acids with an estimated molecular mass of 17.3 kDa. The amino acid sequence of the cDNA is highly homologous to the genes encoding pathogenesis related protein 10 (PR-10) found in other plants. Especially, the nucleotide sequence is almost identical to that of CaPR-10 from *C. annuum* (FIG. 3). So, the clone was named as CbPR-10 for pathogenesis related protein 10 of *C. baccatum*. Based on the nucleotide sequence, the CbPR-10 gene belongs to the PR-10 family. Sequence identity is highest at 98%, 90%, and 83% with PR-10 from *C. annuum*, *C. chinense*, and *Solanum virginianum*, respectively.

The expression pattern of CbPR-10 gene was investigated in the infected fruits of *C. baccatum* with anthracnose fungus and compared with that of CaPR-10 gene in *C. annuum* showing susceptible reaction. RT-PCR analysis was performed with total RNA extracted from infected fruits of both species at various time points (FIG. 4A). CbPR-10 in *C. baccatum* was induced by fungal infection on the first day, peaked on the second day and then declined after inoculation. However, the induced level of CaPR10 in *C. annuum* showed dual expression pattern on the first and third day at much less level.

We examined whether the time-courses of PR-10 accumulation are correlated with anthracnose symptom development on infected fruits. Western blot analysis was performed with soluble proteins extracted from the fruits of both species. Using anti-CaPR-10 antibody, an 18 kDa protein corresponding to PR-10 was detected in the unripe fruits (FIG. 4B). In resistant reaction of *C. baccatum*, immunoblot analysis indicated that the level of 18 kDa increased slightly, 19 kDa band appeared on the first day after the infection with anthacnose fungus and these bands were maintained further in the fruits. In the susceptible reaction of *C. annuum*, however, basal level of CaPR-10 protein decreased significantly on the first day and then increased slightly. Interestingly, 19 kDa band was clearly detectable only in the infected fruits of *C. baccatum* while undetectable in those of *C. annuum*. These data suggest that the phosphorylation of CbPR-10 protein in 19 kDa is related to the resistance response of the fruits of *C. baccatum* against anthracnose fungus.

In previous studies, no lesion formed on the resistant fruit of *C. baccatum* in planta inoculation, but typical anthracnose symptom developed in the infected fruit of *C. annuum* with anthracnose fungus. So, immunohistochemical study was conducted to clarify the accumulation and location of PR-10 proteins in infected fruits of both species. PR-10 proteins are located in the cytosol as expected from the sequence analysis, showing no signal peptide (FIG. 5). Higher accumulation of CbPR-10 was detected in the fruit epidermis of *C. baccatum* and fungal induced accumulation was also much higher in both epidermis and sub-epidermal layers in *C. baccatum* during infection stage.

The recombinant PR-10 proteins expressed in *E. coli* were shown to cleave pepper total RNA, but relative activity of CbPR-10 was much stronger than CaPR-10 (FIGS. 7, 8). To clarify the biological properties of CbPR-10, antifungal activity of recombinant CbPR-10 was investigated. Normal development of the fungus was seriously impaired by the application of the proteins so that fungal hypha tended to elongate and branch and, particularly, appressorium formation was blocked during the fungal development. There was no significant difference in the antifungal activity between CaPR-10 and CbPR-10, but fungal viability was effectively damaged by CbPR-10 than CaPR-10 (FIG. 9).

This invention includes the expression vectors comprising the nucleotide sequence of CbPR-10 associated with a regulatory nucleotide sequence that controls expression of CbPR-10 in a host cell. The host expression vector systems include *E. coli* or plants transformed with recombinant expression vectors.

EXAMPLES

Materials and Methods

Plant materials. *Capsicum baccatum* cv. PBC80, which is identified to be a resistance to *Colletotrichum acutatum*, was used. As a susceptible plant, *C. annuum* cv. Yeo-ju was used. Plants were grown under protected green house conditions at 25° C. Fully grown unripe green fruits of eight month-old pepper plants were used for nucleic acid extraction and pathogen inoculation.

Fungal pathogen and inoculation. Inoculum preparation and artificial inoculation procedures were followed by the methods of Kim et al., (2004) with slight modifications. The Korean isolate of *Colletotrichum acutatum*, KSCa-1, was used as anthracnose pathogen. The isolate was grown on potato dextrose agar (PDA) medium (Sigma, USA) at 25° C. under an alternative 16 h fluorescent light and 8 h dark. The 7-day-old PDA plates were flooded with distilled water and fungal colonies were gently scraped from the plates. Then the suspension was filtered through four layers of cheesecloth to remove mycelial debris. Inoculum concentration was adjusted to $5 \times 10^5$ conidia/mL with a hemacytometer. As a wounding inoculation method, microinjection specialized with a needle with an accurately adjustable wounding depth was used. The detached fruits were washed once with distilled water and were injected with 2 µL of the conidial suspension at usually three sites of fruit epidermis and at a depth of 0.8 mm. The inoculated fruits were placed in an acryl box moistened with four layers of wet kitchen towel. The acryl boxes were tightly sealed with wrap of vinyl chloride to maintain near 100% of relative humidity and incubated at 25° C.

Gene cloning, sequence and gene expression analysis. Total RNA was extracted from infected unripe fruits using RNeasy Plant Kit (Quiagene, Germany) according to the manufacturer's instructions. A forward primer, 5'ATGGGTGCT-TATACCT3' (SEQ ID NO: 5) and a reverse primer, 5'TTAAACATAGACAGAAGGAT3' (SEQ ID NO: 6), were used for RT-PCR. The PCR product of a full-length cDNA was cloned in pGEMT-easy vector (Promega, USA) and sequenced. cDNA sequencing was performed with an ALFexpress automated DNA seqencer (Amersham, UK). Analyses of nucleotide and amino acid sequences were performed with the DNASIS sequence analysis software for Windows, version 2.1 (Hitachi, USA). For a homology search, the cDNA sequences were compared to the sequences in the NCBI nonredundant database using the BLAST electronic server. To determine expression level of PR-10 genes, RT-PCR analysis was conducted using 100 ng of total RNA extracted from infected fruits as template.

Cloning of gDNA by PCR. Coding region of CbPR-10 gene was amplified by PCR from gDNA of *C. baccatum* as template. Primers used were 5'ATGGGTGCTTATACCT3' (SEQ ID NO: 7) and 5'TTAAACATAGACAGAAGGAT3' (SEQ ID NO: 8). Then, to clone upstream region of CbPR-10 gene using inverse PCR, pepper genomic DNA was digested with HindIII, and self-ligated to form circular DNA fragments. These were amplified by PCR using LA or Ex Taq polymerase (TaKaRa, Japan) with a set of primers corresponding to the N-terminal of the PR-10 sequence. Temperature cycles were as follows: 94° C. for 1 min, followed by 30 cycles of 94° C. for 1 min, 60° C. for 3 min, and 70° C. for 1 min. A 1.2 kb PCR product containing parts of the CbPR-10 sequence, was sub-cloned into Topo vector (Invitrogen, USA) and sequenced.

SDS-PAGE, Western blot analysis, and immunohistochemistry. SDS-PAGE was performed with total proteins separated on 12% polyacrylamide gels according to Laemmli (1970) and electrotransferred onto polyvinylidene fluoride (PVDF) membranes. For immunoblot analysis, primary antibody was used at a 1:1500 dilution. A goat anti-rat antibody coupled to alkaline phosphatase was used as secondary antibody at a 1:5000 dilution. The secondary antibody was visualized with luminol (ECL, USA).

For immunolocalization study, pepper fruits were fixed in 1% glutaraldehyde/3% paraformaldehyde in 100 mM sodium phosphate buffer, pH 7.0, dehydrated in ethanol, and embedded in paraffin. Tissues were transverse-sectioned into slices 10 µm in thickness. For immunolabeling, deparaffinized sections were incubated with primary antibody for 12 hours at 12° C. Polyclonal antibody against recombinant CaPR-10 protein was used at a dilution of 1:2000. Control tissues were incubated with pre-immune serum. Then the sections were incubated with biotinylated secondary antibody of goat anti-rat (DAKO, USA). For detection, the secondary antibody was colorized with 3-amino-9-ethylcarbazole according to the manufacturer's instructions (DAKO, USA).

Recombinant CaPR-10 and CbPR-10 proteins. The open reading frame of CaPR-10 or CbPR-10 cDNA were amplified by polymerase chain reaction and inserted in-frame with the glutathione-S-transferase (GST) coding sequence in expression vector pGEX6p-1 (Pharmacia Biotech, Sweden) between an EcoRI and XhoI site. Each GST fusion protein was expressed in *E. coli* and purified according to the manufacturer's instructions. The concentration of protein was determined by the Bradford method (Bradford, 1976). The pure CaPR-10 or CbPR-10 proteins after PreScision Pretease digestion were used for the analyses of ribonuclease and antifungal activities.

Ribonuclease activity of recombinant CbPR-10 protein. RNA degradation assay was carried out according to the method described by Bantignies et al., (2000).

Antifungal activity of CbPR-10 protein. A monoclonal KSCa-1 isolate of *C. acutatum* was cultured on potato dextrose agar (Difco, USA) for 7 days in the dark at 28° C. Spores were harvested and suspended in sterile distilled water. Ten microliters of spore suspension ($5 \times 10^5$ spores per milliliter) was used in drop culture amended with 10 μl of recombinant protein or PBS buffer and applied to cover glasses. The cover glasses were incubated in humidified chamber at 25° C. in the dark for 24 hours. To observe fungal viability, germinated spores were stained with Live/Dead bacterial viability kit (Molecular probe, USA).

Cloning and Sequence Analysis of CbPR-10 cDNA

By using RT-PCR, a cDNA fragment was cloned from the unripe fruits of *Capsicum baccatum* infected with anthracnose fungus, *Colletotrichum acutatum*. A full-length cDNA clone was designated as CbPR-10 (*Capsicum baccatum* pathogenesis related protein 10). The CbPR-10 cDNA is 480 base pairs (bp) long and encodes a predicted protein of 159 amino acids (FIG. 2) with an estimated molecular mass of 18 kilodaltons (kDa). The CbPR-10 protein contains 'P-loof' that is conserved among PR-10 proteins and possesses several putative phosphorylation sites predicted by NetPhos WWW server (FIG. 3). The CbPR-10 protein shares very high homology of 95% identity with CaPR-10 (Park et al., 2004) from *C. annuum* and 61% identity with STH-10 protein from potato (Matton and Brisson, 1989).

Cloning and Sequence Analysis of CbPR-10 gDNA

In internal region of a CbPR-10 gene was cloned by PCR method. The primers were designed based on the nucleotide sequence of CaPR-10 gene because the sequence of CbPR-10 showed 96% of identity with that of CaPR-10 gene. A 1025 bp of amplification product was composed of two exons intervening with an intron sequence and 3' UTR region. Then, inverse PCR (iPCR) was conducted to clone the regulatory region of the gene. A product of 1.3 kb was amplified in the PCR reaction containing *C. baccatum* gDNA digested with HindIII (FIG. 2). The promoter sequence was determined for a region of 1154 bp upstream of the ATG initiation codon. A number of sequences with significant similarity to previously characterized elements in inducible genes were identified such as the SA-responsive element (TCA), elicitor-responsive element (ELI box), heat shock element (HSE), the wound responsive elements (WUN), TATA box, etc.

Induction of PR-10 Gene by Fungal Infection

To assess the expression of PR-10 during fungal infection, spore suspension of anthracnose fungus was inoculated to elicit resistant and susceptible reactions in the unripe fruit of *C. baccatum* and *C. annuum*, respectively. Semi-quantitative reverse polymerase chain reaction (RT-PCR) was conducted in both fruits showing different disease symptom (FIG. 4A). The result shows that the mRNA level of CbPR-10 in *C. baccatum* was induced on the first day, peaked on the second day and then declined after inoculation. However, the induced level of caPR10 in *C. annuum* showed dual expression pattern on the first and third day at much less level.

Induction and Phosphorylation of PR-10 Protein by Fungal Infection

Using anti-PR-10 antibody, an 18 kDa protein corresponding to PR-10 with a predicted size 18 kDa was detected in pepper fruit infected with anthracnose fungus (FIG. 4B). In resistant reaction, immunoblot analysis indicated that the level of CbPR-10 protein increased slightly at the first day after the infection with anthacnose fungus and maintained further in the fruit of *C. baccatum*. In the susceptible reaction, however, basal level of CaPR-10 protein was significantly decreased at the first day and then slightly increased in that of *C. annuum*. The phosphorylated PR-10 protein with a predicted size 19 kDa was clearly detectable in infected fruits of *C. baccatum* while undetectable in those of *C. annuum*. An unknown weak band with a molecular weight of about 20 kDa was cross-reacted with the anti-CaPR-10 antibody in both *C. baccatum* and *C. annuum*. These data suggest that the phosphorylation of CbPR-10 protein is probably related to the resistance response of the fruits of *C. baccatum* against anthracnose fungus.

Immunolocalization of PR-10 Protein in Infected Pepper Fruits

To clarify the localization and accumulation of PR-10 protein during fungal infection, immunohistochemical examination of the protein was conducted with transverse-sections of the fruits of both species. The sections were prepared from infected unripe fruits with anthracnose fungus at 0, 24, 48, and 72 HAI, respectively (FIG. 5). The accumulation of PR-10 protein was localized rarely in outer epidermal cells in both fruits at 0 HAI. After fungal infection, PR-10 accumulation was gradually increased in epidermal cells and sub-epidermal layers of the fruits. However, the amount of the proteins was significantly higher in the fruits of *C. baccatum* than that of *C. annuum*. The results suggest that CbPR-10 protein is localized in the epidermal cell of pepper fruits during normal development. Fungal induced CbPR-10 accumulation was occurred massively in cortical parenchyma cells as well as epidermal cells of the fruits of *C. baccatum*, while much less amount of CaPR-10 protein was observed in the normal or infected fruits of *C. annuum*.

Ribonuclease Activity of Recombinant CbPR-10 Protein

To access the functional activity of CbPR-10 protein, recombinant CbPR-10 protein was expressed in *E. coli*, purified (FIG. 6), and tested for the ribonuclease activity according to the method of Bantignies et al., (2000). The total RNA extracted from the unripe pepper fruits was incubated with recombinant CbPR-10 as well as CaPR-10 or RNase A (SIGMA, USA). RNase A was used as positive control and recombinant CaPR-10 protein was used for the comparison of relative enzyme activities between *C. annuum* and *C. baccatum*. In FIG. 7, relatively stronger enzyme activity of the CbPR-10 was shown as faster migration of degradation products in the agarose gel rather than that of CaPR-10. As another control, RNase A degrades pepper RNA completely under the same condition. FIG. 8 shows relative enzyme activities were compared between CaPR-10 and CbPR-10 during a time course. The result showed that CbPR-10 had much stronger ribonuclease activity than CaPR-10.

Antifungal Activity Between Recombinant CbPR-10 and CaPR-10 Protein

Antifungal activity of recombinant CbPR-10 was investigated to clarify the biological properties of CbPR-10 in plant. To examine the effect of CbPR-10 on the growth of anthracnose fungus, recombinant CbPR-10 protein was amended with the fungal spores. Related activity of CaPR-10 protein was compared as positive control. The spores of fungus start to germinate at 1 hr and develop first appressorium at 6 hrs after deposition of the surface of cover glass. However, normal development of the fungus was severely impaired by the application of recombinant PR-10 protein. At low concentration of the protein, the tip of hypha tended to elongate and branched without developing appressorium (FIG. 9). The germination of the spores was completely blocked at 0.5 mg/ml of both CaPR-10 and CbPR-10 proteins. In addition, the viability of the fungus showing an abnormal growth was examined by staining with Live/Dead bacterial viability kit (Molecular probe, USA). The results showed that viability of the fungus was severely affected as low as 0.05 mg/L of PR-10 protein.

REFERENCES

Bantignies B, Seguin J, Muzac I, Dedaldechamp F, Gulick P, Ibrahim R (2000). Direct evidence for ribonucleolytic activity of a PR-10-like protein from white lupin roots. Plant Mol biol. 42: 871–81

Bradford M M (1976). A rapid and sensitive method for the quantitation of microgram quantities of protein utilizing the principle of protein-dye binding. Anal. Biochem. 72: 248–254

Kim K H, Yoon J B, Park H G, Park E W, Kim Y H (2004). Structural modification and programmed cell death of chili pepper fruit related to resistance responses to *Colletotrichum gloeosporioides* infection. Phytopathology 94: 1295–1304

Laemmli U K (1970). Cleavage of structural proteins during the assembly of the head of bacteriophage T4. Nature 227: 680–685

Matton D P, Brisson N (1989). Cloning, expression, and sequence conservation of pathogenesis-related gene transcripts of potato. Mol Plant Microbe Interact 2: 325–331

Park C-J, Kim K-J, Shin R, Park J M, Shin Y C, Paek K H (2004). Pathogenesis-related protein 10 isolated from hot pepper functions as a ribonuclease in an antiviral pathway. Plant Journal 37: 186–198

What is claimed is:

1. An isolated nucleic acid molecule of SEQ ID NO: 1 encoding the pathogenesis related protein 10 from *Capsicum baccatum*.

2. An expression vector for transformation of *E. coli* or plant cells comprising the polynucleotide of SEQ ID NO: 1 operably linked to regulatory sequences for transcription.

3. An *E coli* cell transformed with the expression vector of claim 2.

4. A transgenic plant cell transformed with the expression vector of claim 2.

5. A transgenic plant grown from the transgenic plant cell of claim 4, having enhanced resistance to anthracnose fungus compared to that of an untransformed plant of the same species.

* * * * *

SEQUENCE LISTING

```
<160> NUMBER OF SEQ ID NOS: 9

<210> SEQ ID NO 1
<211> LENGTH: 480
<212> TYPE: DNA
<213> ORGANISM: Capsicum baccatum
<220> FEATURE:
<221> NAME/KEY: CDS
<222> LOCATION: (1)..(477)

<400> SEQUENCE: 1 atg ggt gcc tat acc ttt act gac aag tcc aca gcc tca gtt gcc cca      48
Met Gly Ala Tyr Thr Phe Thr Asp Lys Ser Thr Ala Ser Val Ala Pro
1               5                   10                  15 tca agg cta ttc aaa gct ttg gtt att gat ttt aac aac att gta tct      96
Ser Arg Leu Phe Lys Ala Leu Val Ile Asp Phe Asn Asn Ile Val Ser
                20                  25                  30 aaa ttg gca cct gat gtt aag agt att gag aat gtt gaa ggt gat ggt     144
Lys Leu Ala Pro Asp Val Lys Ser Ile Glu Asn Val Glu Gly Asp Gly
            35                  40                  45 ggt gct gga acc atc aag aag atg acc ttt gtc gaa ggt ggt cca ata     192
Gly Ala Gly Thr Ile Lys Lys Met Thr Phe Val Glu Gly Gly Pro Ile
        50                  55                  60 aag tac atg aag cac aag att cat gtg att gac gaa aag aat tta gta     240
Lys Tyr Met Lys His Lys Ile His Val Ile Asp Glu Lys Asn Leu Val
65                  70                  75                  80 aca aaa tat tca ctt atc gaa agt gat gtt ctt gaa ggc aaa gca gaa     288
Thr Lys Tyr Ser Leu Ile Glu Ser Asp Val Leu Glu Gly Lys Ala Glu
                85                  90                  95 tca gtt gat tat gat ggc aaa ttt gaa gct tct gca gat gga gga tgt     336
Ser Val Asp Tyr Asp Gly Lys Phe Glu Ala Ser Ala Asp Gly Gly Cys
                100                 105                 110 gtt tgc acc aca gta act gtg tac aac aca aaa ggt gat tat gtt gtt     384
Val Cys Thr Thr Val Thr Val Tyr Asn Thr Lys Gly Asp Tyr Val Val
            115                 120                 125 act gag gaa gaa cac aat gtg cac aaa gac aaa gcc aat gac ctt ctc     432
Thr Glu Glu Glu His Asn Val His Lys Asp Lys Ala Asn Asp Leu Leu
        130                 135                 140 aag gcc atc gaa gca tac ctc ctc gcc aat cct tct gtc tgt gtt taa     480
Lys Ala Ile Glu Ala Tyr Leu Leu Ala Asn Pro Ser Val Cys Val
145                 150                 155
```

<210> SEQ ID NO 2
<211> LENGTH: 159
<212> TYPE: PRT
<213> ORGANISM: Capsicum baccatum

<400> SEQUENCE: 2

```
Met Gly Ala Tyr Thr Phe Thr Asp Lys Ser Thr Ala Ser Val Ala Pro
1               5                   10                  15

Ser Arg Leu Phe Lys Ala Leu Val Ile Asp Phe Asn Asn Ile Val Ser
            20                  25                  30

Lys Leu Ala Pro Asp Val Lys Ser Ile Glu Asn Val Glu Gly Asp Gly
        35                  40                  45

Gly Ala Gly Thr Ile Lys Lys Met Thr Phe Val Glu Gly Gly Pro Ile
    50                  55                  60

Lys Tyr Met Lys His Lys Ile His Val Ile Asp Glu Lys Asn Leu Val
65                  70                  75                  80

Thr Lys Tyr Ser Leu Ile Glu Ser Asp Val Leu Glu Gly Lys Ala Glu
                85                  90                  95

Ser Val Asp Tyr Asp Gly Lys Phe Glu Ala Ser Ala Asp Gly Gly Cys
            100                 105                 110

Val Cys Thr Thr Val Thr Val Tyr Asn Thr Lys Gly Asp Tyr Val Val
        115                 120                 125

Thr Glu Glu Glu His Asn Val His Lys Asp Lys Ala Asn Asp Leu Leu
    130                 135                 140

Lys Ala Ile Glu Ala Tyr Leu Leu Ala Asn Pro Ser Val Cys Val
145                 150                 155
```

<210> SEQ ID NO 3
<211> LENGTH: 1157
<212> TYPE: DNA
<213> ORGANISM: Capsicum baccatum
<220> FEATURE:
<221> NAME/KEY: promoter
<222> LOCATION: (1)..(1157)

<400> SEQUENCE: 3

```
aagcttctta aaacagtata tccatgaatc tgcttgactt gtttcatgtc attttctcaa     60
tcatcaaaga actcaacaat ctttaatgtc atgcacacaa taaattttga gtatgaatat    120
ctaatttaaa gaaaaaatta tatttaatta gtgcaagatt ttacatattt ttatttataa    180
cagctaaata gaaaatttga acgtcaaacg ttttacatat ataatagtag ctctctatag    240
caacagttct aaatttttaa atatacatta tcattataaa gaggttttac tgtataaata    300
aaaatctcga tcaaaacatc attaaatgca aactcatgag actgtagcat tcatcttttg    360
aatgatagta ataaataatt ttgaattcta gctgttcata ccatatactg agaataatat    420
cagcctacca ctattgaaaa ccaagttgat aggttcccac agtctacatc aacttaatat    480
cgtgtcagca aatcttattg ttatttatca tttggcataa aattctctca atatgtatca    540
tgactaacaa attaattatg gcacaacatc tagaagaaag aaaaactgaa cccaaatgtc    600
agcaatggag tgctttgaat gttgaaatta agactaaatt aaggttgctc aagagtgaac    660
tctaagggtg tgcttggtat gtatgagaga aaaacatttt caatcaaata atattttctt    720
caaaaataag tggggttttt cgtgtcttga caaaaaatgta taaaaatatt atccaaatat    780
atttatatat tttttctttt agatcatgtt aagtgaattg ttgagatctt aatcctattt    840
tttgaaaaat agactatttt caatacactt ttgatttaag taaaacattt taaatcgaac    900
```

-continued

```
ttgaaaagaa aatacaataa tgaagatatc atattaaaaa aaaaaaaaag aaatttgttt    960
ttctaagaga atattaattt tgactaacta aacaatcatg tgaagaattt tcaaacacac   1020
cctaaaatct cactacattt tatcactata aataccatct aaaaactccc atatatcaca   1080
cacctcaaaa cattacaatc atcttatcct aagctctttc ttcttcttgt ttaaggcaaa   1140
ttaatcaaag cattatg                                                 1157

<210> SEQ ID NO 4
<211> LENGTH: 159
<212> TYPE: PRT
<213> ORGANISM: Capsicum annuum

<400> SEQUENCE: 4

Met Gly Ala Tyr Thr Phe Thr Asp Lys Ser Thr Ala Ser Val Ala Pro
1               5                  10                  15

Ser Arg Leu Phe Lys Ala Leu Val Ile Asp Phe Asn Asn Leu Val Ser
            20                  25                  30

Lys Leu Ala Pro Asp Val Lys Ser Ile Glu Asn Val Glu Gly Asp Gly
        35                  40                  45

Gly Ala Gly Thr Ile Lys Lys Met Thr Phe Val Glu Gly Gly Pro Ile
    50                  55                  60

Lys Tyr Met Lys His Lys Ile His Val Ile Asp Glu Lys Asn Leu Val
65                  70                  75                  80

Thr Lys Tyr Ser Leu Ile Glu Ser Asp Val Thr Glu Asn Lys Ala Glu
                85                  90                  95

Ser Val Asp Tyr Asp Gly Lys Phe Glu Ala Ser Ala Asp Gly Gly Ser
            100                 105                 110

Val Cys Thr Thr Val Thr Val Tyr Asn Thr Lys Gly Asp Tyr Val Val
        115                 120                 125

Thr Glu Glu His Asn Val His Lys Glu Lys Ala Asn Asp Leu Leu
    130                 135                 140

Lys Ala Ile Glu Ala Tyr Leu Leu Ala Asn Pro Ser Val Tyr Val
145                 150                 155

<210> SEQ ID NO 5
<211> LENGTH: 16
<212> TYPE: DNA
<213> ORGANISM: Artificial
<220> FEATURE:
<223> OTHER INFORMATION: Primer

<400> SEQUENCE: 5
atgggtgctt atacct                                                    16

<210> SEQ ID NO 6
<211> LENGTH: 20
<212> TYPE: DNA
<213> ORGANISM: Artificial
<220> FEATURE:
<223> OTHER INFORMATION: Primer

<400> SEQUENCE: 6
ttaaacatag acagaaggat                                                20

<210> SEQ ID NO 7
<211> LENGTH: 16
<212> TYPE: DNA
<213> ORGANISM: Artificial
<220> FEATURE:
```

<223> OTHER INFORMATION: Primer

<400> SEQUENCE: 7
atgggtgctt atacct                                                        16

<210> SEQ ID NO 8
<211> LENGTH: 20
<212> TYPE: DNA
<213> ORGANISM: Artificial
<220> FEATURE:
<223> OTHER INFORMATION: Primer

<400> SEQUENCE: 8
ttaaacatag acagaaggat                                                    20

<210> SEQ ID NO 9
<211> LENGTH: 2200
<212> TYPE: DNA
<213> ORGANISM: Capsicum baccatum

<400> SEQUENCE: 9

| | | | | | |
|---|---|---|---|---|---|
| aagcttctta | aaacagtata | tccatgaatc | tgcttgactt | gtttcatgtc | attttctcaa     60 |
| tcatcaaaga | actcaacaat | ctttaatgtc | atgcacacaa | taaattttga | gtatgaatat    120 |
| ctaatttaaa | gaaaaaatta | tatttaatta | gtgcaagatt | ttacatattt | ttatttataa    180 |
| cagctaaata | gaaaatttga | acgtcaaacg | ttttacatat | ataatagtag | ctctctatag    240 |
| caacagttct | aaattttaa  | atatacatta | tcattataaa | gaggttttac | tgtataaata    300 |
| aaaatctcga | tcaaaacatc | attaaatgca | aactcatgag | actgtagcat | tcatcttttg    360 |
| aatgatagta | ataataatt  | ttgaattcta | gctgttcata | ccatatactg | agaataaat     420 |
| cagcctacca | ctattgaaaa | ccaagttgat | aggttcccac | agtctacatc | aacttaatat    480 |
| cgtgtcagca | aatcttattg | ttatttatca | tttggcataa | aattctctca | atatgtatca    540 |
| tgactaacaa | attaattatg | gcacaacatc | tagaagaaag | aaaaactgaa | cccaaatgtc    600 |
| agcaatggag | tgctttgaat | gttgaaatta | agactaaatt | aaggttgctc | aagagtgaac    660 |
| tctaagggtg | tgcttggtat | gtatgagaga | aaaacatttt | caatcaaata | atattttctt    720 |
| caaaaataag | tggggttttt | cgtgtcttga | caaaaatgta | taaaaatatt | atccaaatat    780 |
| atttatatat | tttttctttt | agatcatgtt | aagtgaattg | ttgagatctt | aatcctattt    840 |
| tttgaaaaat | agactatttt | caatacactt | ttgatttaag | taaaacattt | taaatcgaac    900 |
| ttgaaaagaa | aatacaataa | tgaagatatc | atattaaaaa | aaaaaaaaag | aaatttgttt    960 |
| ttctaagaga | atattaattt | tgactaacta | aacaatcatg | tgaagaattt | tcaaacacac   1020 |
| cctaaaatct | cactacattt | tatcactata | aataccatct | aaaaactccc | atatatcaca   1080 |
| cacctcaaaa | cattacaatc | atcttatcct | aagctctttc | ttcttcttgt | ttaaggcaaa   1140 |
| ttaatcaaag | cattatgggt | gcctatacct | ttactgacaa | gtccacagcc | tcagttgccc   1200 |
| catcaaggct | attcaaagct | ttggttattg | attttaacaa | cattgtatct | aaattggcac   1260 |
| ctgatgttaa | gagtattgag | aatgttgaag | gtgatggtgg | tgctggaacc | atcaagaaga   1320 |
| tgacctttgt | cgaaggtttg | ttttttattt | tttttgagg  | tgcgatattc | atattaaagg   1380 |
| tcggttatta | gtagccaaaa | ttgatacacg | tgaaattttg | tcagaatatt | ttgaataag    1440 |
| acatttttt  | taatttgata | tttgtatata | gcgatcataa | taagaaaac  | agttttataa   1500 |
| ggtactaaaa | attatacaag | aacaaataaa | ttaattggac | aaatttgatt | gtgactccca   1560 |
| ttttaatcca | tatcaatcca | attatggacg | gctcaaaacc | tacttatata | tttacttaac   1620 |

-continued

| | |
|---|---|
| ctattttgat ctgtccaaat tcaatccatt ccgctcattt aatacttcta tcaataaata | 1680 |
| tccattgaag gatcatttta atagaaaaaa ttatttacct taatatatga aacttaatgt | 1740 |
| ttttttatta atgacaggtg gtccaataaa gtacatgaag cacaagattc atgtgattga | 1800 |
| cgaaaagaat ttagtaacaa aatattcact tatcgaaagt gatgttcttg aaggcaaagc | 1860 |
| agaatcagtt gattatgatg gcaaatttga agcttctgca gatggaggat gtgtttgcac | 1920 |
| cacagtaact gtgtacaaca caaaaggtga ttatgttgtt actgaggaag aacacaatgt | 1980 |
| gcacaaagac aaagccaatg accttctcaa ggccatcgaa gcatacctcc tcgccaatcc | 2040 |
| ttctgtctgt gtttaagcca atgaccttgc tgtgatgtta tatagttaaa taattataag | 2100 |
| tgtgtcatgt ttaagaagtt taaagttttt agatgagagg aaaaaataag attgattatg | 2160 |
| tatgggttgt atcagttctt ctaagggatt gagttttggg | 2200 |